US005689246A

United States Patent [19]

Dordick et al.

[11] Patent Number: 5,689,246

[45] Date of Patent: Nov. 18, 1997

[54] INTRAORAL COMMUNICATION SYSTEM

[75] Inventors: Rowan L. Dordick, Briarcliff Manor, N.Y.; Edwin J. Selker, Palo Alto, Calif.

[73] Assignee: International Business Machines Corporation, Armonk, N.Y.

[21] Appl. No.: 749,044

[22] Filed: Nov. 14, 1996

Related U.S. Application Data

[63] Continuation of Ser. No. 414,410, Mar. 31, 1995, abandoned.

[51] Int. Cl.[6] .......... H04Q 7/00

[52] U.S. Cl. .......... 340/825.19; 340/825.56; 340/825.72

[58] Field of Search .......... 340/825.19, 825.56, 340/825.69, 825.72, 825.64, 407.2; 341/21, 22, 176; 455/100, 41; 400/87; 434/112, 113; 381/70

[56] References Cited

U.S. PATENT DOCUMENTS

| | | | |
|---|---|---|---|
| 3,795,281 | 3/1974 | Chloran | 173/30 |
| 4,539,699 | 9/1985 | Katz et al. | 381/70 |
| 4,605,927 | 8/1986 | Katz et al. | 340/825.19 |
| 4,616,213 | 10/1986 | Danish | 341/21 |
| 4,629,424 | 12/1986 | Lauks et al. | 433/6 |
| 4,728,812 | 3/1988 | Sheriff et al. | 307/134 |
| 4,746,913 | 5/1988 | Volta | 340/706 |
| 4,783,656 | 11/1988 | Katz et al. | 340/825.19 |
| 5,212,476 | 5/1993 | Maloney | 340/825.19 |
| 5,233,662 | 8/1993 | Christensen | 387/70 |
| 5,460,186 | 10/1995 | Buchhold | 340/825.19 |
| 5,523,745 | 6/1996 | Fortune | 340/825.19 |

FOREIGN PATENT DOCUMENTS

| | | | |
|---|---|---|---|
| A-0487027 | 5/1992 | European Pat. Off. . | |
| A-0621021 | 10/1994 | European Pat. Off. . | |
| A-660554 | 5/1987 | Switzerland . | |
| A-2094949 | 9/1982 | United Kingdom . | |
| 2145257 | 3/1985 | United Kingdom | 340/825.19 |
| WO-A-9007249 | 6/1990 | WIPO . | |

*Primary Examiner*—Edwin C. Holloway, III

*Attorney, Agent, or Firm*—Daniel P. Morris; Alvin J. Riddles

[57] ABSTRACT

An intraoral interactive communication system wherein through a mouthpiece tongue pressure coded electrical signals are delivered to a processor. The mouthpiece is constructed to conform to the shape of the roof of the mouth, and is positioned behind the upper teeth. The mouthpiece is laminar in structure with an array of pressure responsive locations. A separate pressure responsive location is provided which may actuate a head aimed light. A display is connected to the processor and viewable by the human communicator providing feedback to the communicator.

7 Claims, 2 Drawing Sheets

1
2
3
4
5
6
7
8
9
10
11
12
13
14
15
16
17
18
19
20
21
22
23
24
25
26
27
28
29
30
31
32
33
34
35
36

1
2
3
4
6
7
9
10
12
13
24
25
27
28
30
31
35
38

1
2
3
4
6
24
33
36
38
39

7
16
25
38
39
40
41
42
43
44
45
46

LIGHT RESPONSIVE ELEMENT
56
55
50
1
33
3
54
COMPUTER MONITOR 52
57
58
51
POWER AND RELAY
COMPUTER PROCESSOR
53

21
15
18
60
4
34

16
19
22
33
17
24
23
3

63
61
38
16
40
44
41
62
60
39
25

15
18
21
61
4
16
19
22
34
33

3
17
20
23

INTRAORAL COMMUNICATION SYSTEM

This application is a continuation of application Ser. No. 08/414,410, filed Mar. 31, 1995, now abandoned.

FIELD OF THE INVENTION

The invention is in the field of communication systems and in particular to a communication system where a device held in the oral cavity of a human facilitates interactive communication.

BACKGROUND OF THE INVENTION AND RELATION TO THE PRIOR ART

Situations are arising in the communication arts where it is becoming advantageous for a human to be able to communicate and control apparatus without using the normal audio or manual means. Such situations frequently arise where the human is unable, due to a handicap, to use the normal communicating means or where the human is engaged in a task that requires full use of manual or other capabilities.

There has been effort in the art to provide communicating ability through devices held in the oral cavity and employing the use of tongue movement, jaw movement and/or head movement. These devices have come to be known in the art as intraoral controllers. In U.S. Pat. No. 4,605,927 the tongue is used to provide switch actuation with communication to a remote apparatus by an intraoral power supply and FM transmitter. In U.S. Pat. No. 4,728,812 the use of the jaw movement is employed to actuate a potentiometer. In U.S. Pat. No. 5,233,662 the tongue is used to interrupt light beams in the mouthpiece with the result being communicated by an audio or light signal from the mouthpiece. In U.S. Pat. No. 5,212,476, electrical signals produced from ion exchange in tongue muscle contraction are communicated through a transceiver. In IBM TDB 32, May 12, 1990, pages 445–447 the tongue is employed to block codable combinations of air holes in a mouthpiece with the results being communicated by the effect of the change in air flow on a remote plurality of pressure transducers and wherein the codable combinations of air holes permits a broad range of expository information.

SUMMARY OF THE INVENTION

An intraoral communication system that includes a mouthpiece in which selectable, individual and combinations, of tongue distinguishable pressure responsive discrete locations, are caused to produce signals by compression between a force supplied by the tongue and an opposing force supplied by the support for the mouthpiece provided by the roof of the mouth. The signals are delivered by cable or transmission via light or radio frequency to a communication and control device such as a computer, with feedback to the communicating person available through a monitor.

DESCRIPTION OF THE INVENTION

In communication situations where the conventional use of hands, arms and voice are unavailable or are restricted, such as, where the potential communicator is physically handicapped or where the potential communicator is performing tasks where the usual manner of communication is unavailable or already in service; the invention provides a system that permits the human doing the communicating to communicate interactively, that is to communicate both expository type information which is constructed type information and selection type information which is prompted type information.

Expository type capability is provided by a mouthpiece positioned in the mouth and conforming to the shape of the hard palate or roof of the mouth in which selectable combinations of tongue distinguishable pressure responsive discrete locations are caused to generate signals by being compressed by the force of tongue pressure. The tongue distinguishable pressure responsive locations individually and in various combinations provides the communicating human with the ability to construct a wide range of expository type information.

Selection type information communicating capability is provided by a separate signalling capability actuated by tongue pressure on a specific tongue pressure location. One such signalling capability is through a light source attached to the mouthpiece extending through the lips, aimed by head movement and which is turned on by tongue pressure on a separate pressure responsive location.

The communication system of the invention makes possible a direct and interactive exchange of information between a communicating human and a control system including an information processing system. In FIGS. 1–4 there are top, cross sectional and perspective views of the structure and features of a mouthpiece element implementing the principles of the invention.

Figure 1:
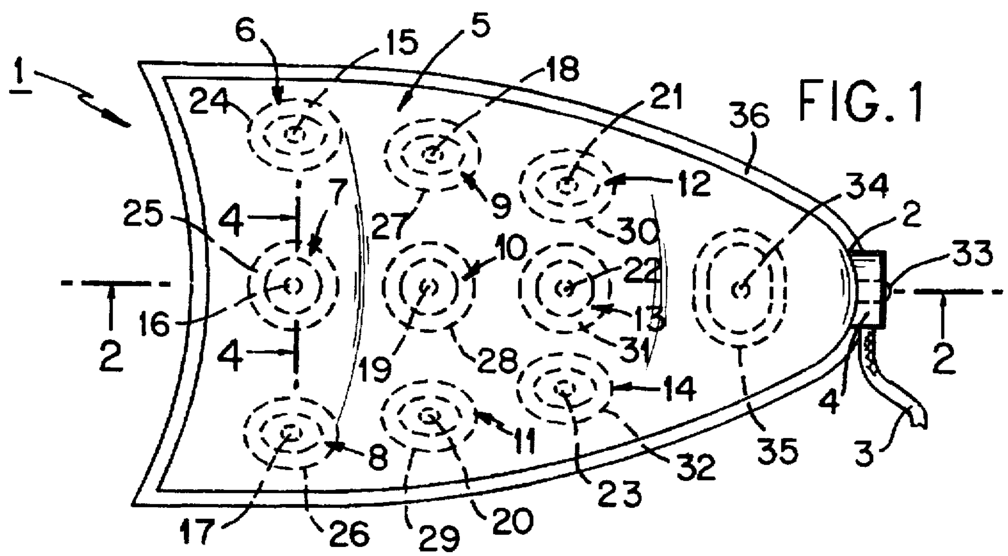
FIG. 1 is a top view of the intraoral mouthpiece element of the invention.

In the intraoral communication system there is a mouthpiece of the invention. The mouthpiece will be adjacent to the roof of the mouth when in position. It is a laminated, wiring and pressure responsive member of the system, containing structure, shaped to conform to the roof of the mouth, positioned behind the upper teeth, hermetically sealed around the edges and which is provided with one or more of the following: a plurality of tongue distinguishable, tongue pressure responsive discrete locations, a cable entry capable of supplying power and signals, a small power supply, a signal processing chip and a light pen or light source that extends through the teeth and lips. Referring to FIG. 1 an embodiment of the invention is shown wherein the mouthpiece 1 has a region 2 that conforms to the region of the mouth behind the upper teeth, not shown, and supports an external cable 3 holder 4 that is attached to the mouthpiece 1 and extends through the upper and lower teeth and lips, not shown. In the area 5 of the mouthpiece 1 there are positioned, spaced, pressure responsive, locations 6–14 each containing within the laminations of the structure a pressure responsive electrical signal device labelled elements 15–23. On the underside, or the side that will be adjacent to the tongue when the mouthpiece 1 is in position, there are corresponding protuberances or bumps 24–32 that provide the tongue with location distinguishing capability and which assist in translating gross tongue pressure to focus on the pressure responsive signal device at the particular location. In practice three rows of three each of pressure responsive locations provide an extensive number of permutations and combinations correlatable with a substantial number of expository statements.

An aiming signaling capability is provided by a light pen or light source 33 that together with tongue distinguishable switching permits head movement to aim the light and the tongue to turn it on. In FIG. 1 the aiming switch 34 is in the area behind the upper teeth in a location separated from the locations 6–14 and the tongue distinguishing ability of it is enhanced by providing a different elongated shaped bump 35, as shown.

The laminated structure of the mouthpiece 1 is hermetically sealed, labelled symbolically an element 36, around the edges and around the holder 4. An electrical communication cable 3 extends out of the mouthpiece 1 to power supply and signal processing and transmission elements of the system, not shown in this figure.

Figure 2:
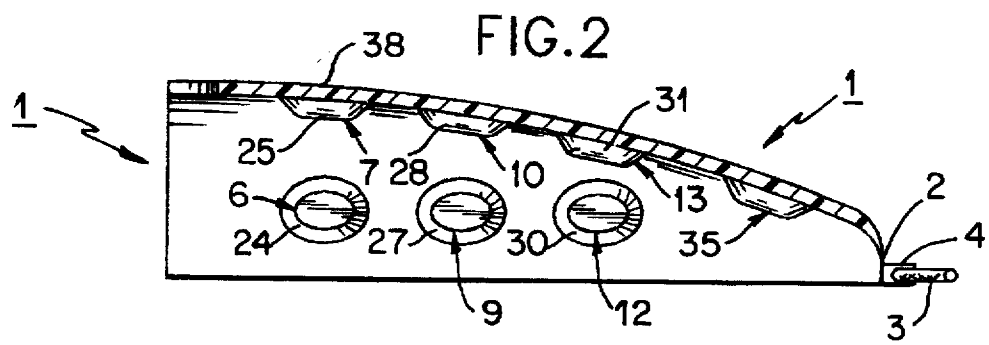
FIG. 2 is a side view along the line 2—2 of FIG. 1, of the mouthpiece element of FIG. 1.

Referring to FIG. 2 there is shown a cross sectional view of the mouthpiece 1 along the lines 2—2 of FIG. 1 using the same reference numerals for like elements as used in FIG. 1. In position, the mouthpiece 1 has the upper surface 38 in contact with the roof of the mouth, not shown, with the region 2 behind the upper teeth, not shown, and with the cable 3 holder 4 between the teeth, not shown. The bumps, 24–32 of FIG. 1, of which 24, 25, 27, 27, 30, 31 and 35 are visible in FIG. 2, each extending from the surface 39, are readily distinguishable by the tongue and the force of pressure applied by the tongue is opposed by the opposing support force of the mouthpiece against the roof of the mouth.

Figure 3:
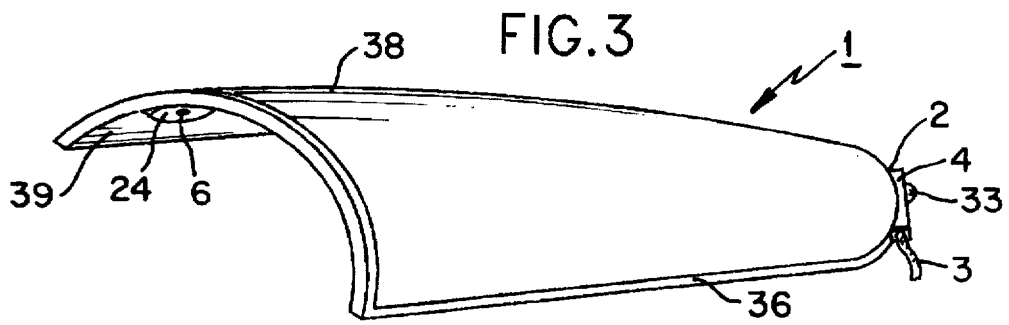
FIG. 3 is a perspective view of the mouthpiece element of FIGS. 1 and 2.

Referring to FIG. 3 a perspective view is shown of the mouthpiece 1 of FIGS. 1 and 2 in which the same reference numerals for like elements as used in FIGS. 1 and 2 are employed. The perspective illustrates the tongue distinguishability of the particular location 6 of a bump 24 on the surface 39 adjacent the tongue.

Figure 4:
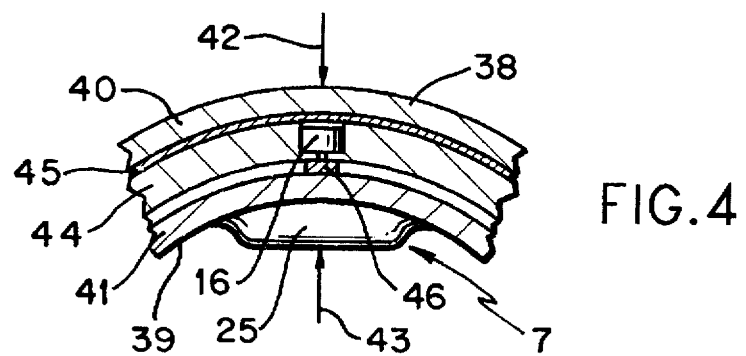
FIG. 4 is a cross sectional view along the line 4—4 of FIG. 1 of the mouthpiece element of FIG. 1.

Referring to FIG. 4, a cross sectional view along the line 4—4 of FIG. 1 is provided of a pressure responsive location, using location 7 as an example and using the same reference numerals for like elements as used in FIGS. 1 and 2 and 3. In FIG. 4 there are external layers 40 and 41 that serve to encapsulate and structurally support the wiring and pressure responsive elements at the particular locations. The layer 40 is supported, as shown by illustrative arrow 42 representing the opposing force to that of the tongue, not shown, as shown by illustrative arrow 43, by the roof of the mouth. The material of the layer 40 can be of rigid material such as the acrylic plastics used in dental orthodontic appliances, molded to the configurations of the roof of the individual mouth, or it can be of a mouth environment resistant non toxic type of material that will provide some flexibility but also providing conformance to the general shape shown in FIG. 3. The layer 41 requires some resilience to permit transfer of tongue pressure, as illustrated by illustrative arrow 42, applied to bump 25 on surface 39, to the pressure responsive element 16. The polyurethane type material available in the art for medical purposes is satisfactory for these requirements.

The pressure responsive element 16 may be of two general types; those having an "open and closed" type of switch property that provides electrical continuity between normally separated conductors that are caused to touch under pressure; and those that provide a quantitative measure of the pressure such as a strain guage or force sensing member. The pressure responsive element 16 is positioned in an opening in an electrically insulating layer 44 that retains the position of the element 16, and provides structural support for the conductors. Conductors 45 and 46 are shown in orthogonal relationship each providing electrical continuity to a contact of the pressure responsive element 16.

Figure 5:
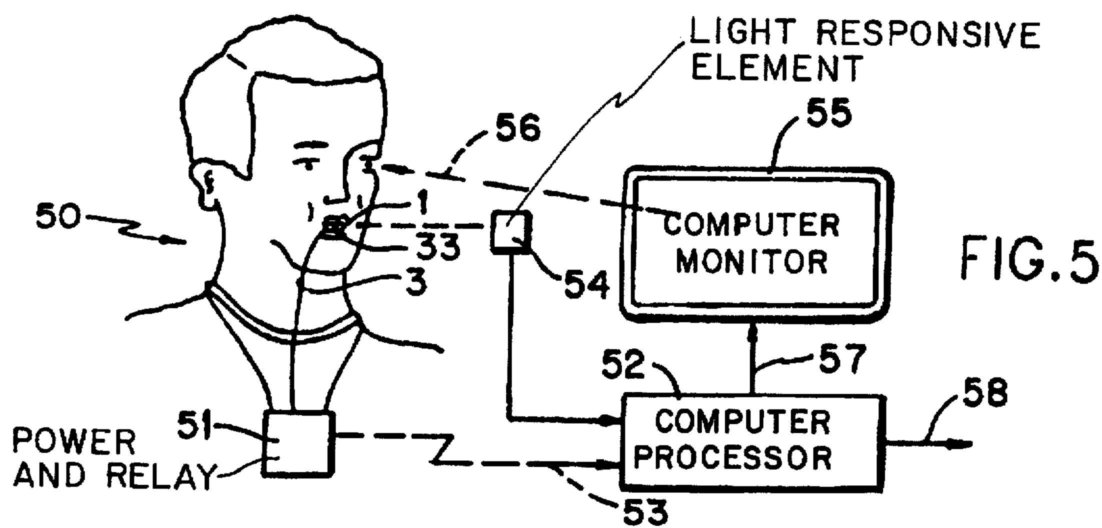
FIG. 5 is a block schematic diagram depicting the human interaction with the elements in the communication system of the invention.

The interrelated structural and physical capabilities of the mouthpiece 1 are integrated into a communication system having extensive capabilities. In FIG. 5 there is shown a block schematic diagram depicting the human interaction with the elements in the communication system of the invention, using the same reference numerals as in previous figures where appropriate. The communication system of the invention provides, through codification of multiple location pressure events, the capability of interactive selection type information transmission together with expository type information transmission between a human communicator and a control apparatus.

Referring to FIG. 5, the mouthpiece 1 is positioned in the mouth of the human 50 doing the communicating, with the cable 3 holder 4 with the light pen or light source 33 extending out of the lips. At least power, and optionally decoding and relay transmission, is provided by element 51 supported by a necklace worn by the human 50 doing the communicating. The element 51 relays the pressure signals from the pressure responsive elements 15–23 and 34 to a processor 52 by communication techniques standard in the art such as Frequency Modulated (FM) radiation or coded infra red (IR) light, shown symbolically as dashed arrow 53. The light from light 33, turned on by tongue pressure on element 34, is pointed by movement of the head of the human 50 doing the communicating to a selected light responsive element which in turn communicates to the controller 52. A computer monitor 55 provides display capability for information feedback to the communicator 50 and for apparatus control standard in the art. There is an optical feedback communication channel shown as a dotted line labelled 56 from the monitor 55 to the communicator 50. By observation of the monitor 55 the communicator 50 can construct responses to be communicated through the mouthpiece 1. The electrical communication channel between the monitor 55 and the processor 52 is symbolically shown as arrow 57. An output from the processor 52 to an apparatus to be controlled is symbolically shown as an arrow labelled element 58. The communication of the invention will also accommodate IR coded light and sonic signalling.

Figure 6:
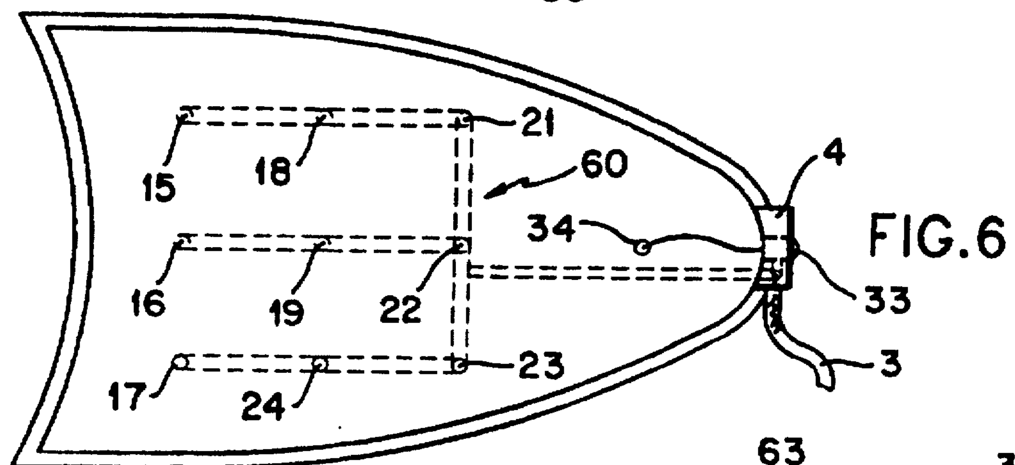
FIGS. 6 and 7 are example wiring patterns for the pressure responsive locations in the preferred embodiment of the mouthpiece element of the invention.
Figure 7:
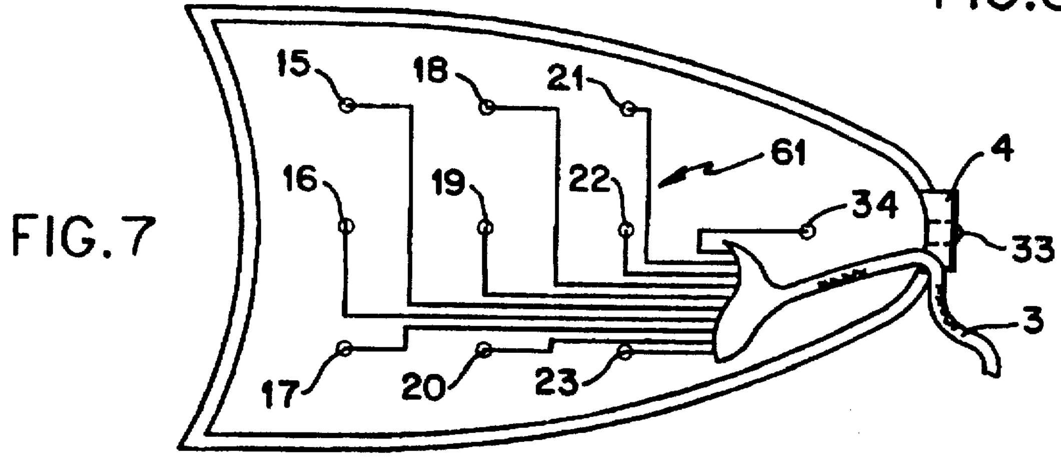

It will be apparent that a wide range of variations in structure and arrangement is possible with the interactive capabilities provided by the invention. As an example, the system in FIG. 5 is described for clarity of function in terms of separate elements 51, 52 and 55, whereas in practice elements 52 and 55 could be a single computer unit connected by a longer cable 3, assuming long cable lengths can be tolerated by the human 50 doing the communicating. It is also possible to provide power and some processing in the mouthpiece. It is further possible to perform processing and codification in the mouthpiece 1 to permit a light source such as 33 to provide infra red (IR) light communication to the controller 52. FIGS. 6 and 7 are example wiring patterns for the pressure responsive locations and FIG. 8 is a cross sectional view of a pressure responsive element location along the line 4—4 of FIG. 1, in a preferred embodiment of the mouthpiece 1 of the invention, wherein the same reference numerals as in previous figures are used where appropriate.

Figure 8:
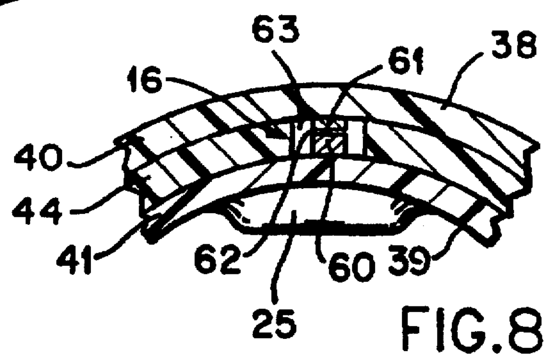
FIG. 8 is a cross sectional view along the line 4—4 of FIG. 1, of a pressure responsive location in the mouthpiece element of the invention.

Referring to FIGS. 6, 7 and 8, in FIG. 6 a top view is shown of a common conductor connecting pattern 60, with connection to a common cable 3 conductor, such as would be used where each pressure responsive element 15–23 is a switch connecting to a common electrical level. Pressure responsive element 34 is the actuator for light 33 which in turn in an IR light emitting diode standard in the art. Element 34 is connected to light 33 with a discrete connection and the remaining terminal of light 33 is connected to the connecting pattern 60. The connecting pattern 60 is made using standard in the art deposition techniques such as silk screening followed by plating to desired current carrying capacity. The pattern 60 is placed on the reverse side of layer 41 of FIG. 8 from the exposed side 39 with the bump 25.

Referring to FIG. 7 a top view is provided of a discrete wiring pattern 61 for the light 33, and pressure responsive elements 15–23 and 34, wherein the conductors come from the cable 3 to the individual pressure responsive locations 15–23 and 34. The wiring 61 of FIG. 7 is placed on the layer 40 in FIG. 8 on the side that is opposite to the exposed side 38. The insulating layer 44, shown only in the cross section in FIG. 8 separates the layers of FIGS. 6 and 7 and has a thickness that produces a separation 62 of about 0.1 millimeter when there is not tongue pressure on bump 25. The opening 63 surrounding the intersection of the conductors 61 and 62 in the layer 44 is about 0.05 millimeters, sufficient to permit the layer 41 to flex under tongue pressure to close the separation 62. The mouthpiece 1 has some flexibility with the layers 40 and 41 being made of polyurethane type material hermetically sealed, by fusion techniques standard in the art, around the edges and in the general shape of FIG. 3. The use of the common wiring pattern of FIG. 6 together with the discrete wiring pattern reduces the number of conductors needed in the cable 3 to less than 15.

What has been described is an intraoral communication system wherein the tongue pressure of the communicating person on locations in a mouth piece delivers coded expository information. Tongue pressure on a separate location of the mouth piece actuates selection information communication. The communicating person receives information through a computer monitor. The combined types of information being useable in interaction with information processing and control devices.

What is claimed is:

1. An intraoral communication mouthpiece comprising in combination:

a laminated portion of edge sealed, mouth environment resistant material that fits in the mouth of a communicating human and a communication portion extending through the teeth of said communicating human, said laminated portion having first and second faces, said first face of said laminated portion conforming to the shape of the roof of the human mouth in the region behind the upper teeth, and, said second face of said laminated portion having an array of rows of tongue locatable and pressure responsive bumps, each having a first shape, and a separately positioned tongue locatable and pressure responsive bump having a second shape that is different from said first shape said laminated portion having within the laminations thereof, pressure responsive, signal members, corresponding to said array of bumps, each of said signal members having conductor means extending to said communication portion, and, said communication portion having a light with actuation of said light being by a separate conductor from said second shaped bump.

2. Intraoral controller communication apparatus comprising in combination:

a mouthpiece with a communication means including a light and electrical conductor means extending through the teeth, said mouthpiece having first and second faces, said first face conforming to the area and the shape of the roof of the human mouth in the region behind the upper teeth, said mouthpiece having tongue distinguishable, tongue pressure responsive, signal members, with signal conducting wiring to each signal member in an array of rows positioned in said area of said roof of said mouth, and a signal member and bump separate from said array and having a different shape from that of said bumps in said rows, serving as a tongue pressure responsive separate actuation member for said light in said communication means, said second face of said mouthpiece having a tongue guiding bump coinciding with each said signal member, said mouthpiece having electrical signal communication means for communicating signals representative of signals from said tongue pressure responsive signal members to a processor location, display means positioned within the view of a communicating human with said mouthpiece, said display means displaying information to said communicating human, and, processing means, responsive to at least one of electrical and light signals from said mouthpiece, providing display information to said display means and providing control signals.

3. The apparatus of claim 2 including a member supported by the neck of said communicating human and providing at least one of the functions of power supply and signal relay.

4. The apparatus of claim 2 wherein the functions of said display means and said processing means are in a single computer member.

5. The apparatus of claim 3 wherein the functions of said display means and said processing means are in a single computer member.

6. An intraoral interactive communication system comprising in combination:

display means, positioned to be visible to a communicating human, mouthpiece apparatus positioned in the mouth of said communicating human comprising, a laminated member of edge sealed, mouth environment resistant, material, said laminated member having first and second faces, said first face of said laminated member conforming to the shape of the roof of the human mouth in the region behind the upper teeth, and, said second face of said laminated member having an array of rows of tongue location indicating and pressure responsive actuation first shaped bumps, said array also including a separately positioned tongue distinguishable second and differently shaped pressure responsive actuation bump, said laminated member having a communication portion extending through the upper and lower teeth, said communication portion having a light, said communication portion conveying tongue bump actuation pressure information from said mouthpiece through said teeth, said laminated member having within the laminations thereof, an array of pressure responsive, signal members, corresponding to said array of bumps, each of said signal members having conductor means extending to said communication portion with a separate conductor from said second shaped bump to said light, and, signal processing means responsive to signals from said mouthpiece providing at least display and control output signals.

7. The process of communicating, comprising the steps of:

providing both electrical and optical signals delivered by a communicating person to a processor, through a tongue pressure responsive mouthpiece positioned in the mouth of said communicating person, said mouthpiece having a communicating portion extending through the teeth of the communicating person, providing control of said electrical and optical signals through an array of tongue distinguishable tongue pressure responsive signal generating elements positioned in rows in a first area of said mouthpiece, and by a differently shaped tongue distinguishable tongue pressure responsive, optical signal controlling, signal generating element, positioned in a second area of said mouthpiece separate from said first area of said mouthpiece, providing a display positioned to be viewable by said communicating person, and, processing both said electrical and said optical signals to provide display information at least for said communicating person and to develop control signals.

* * * * *